(12) United States Patent
Hapiot et al.

(10) Patent No.: US 9,556,402 B2
(45) Date of Patent: Jan. 31, 2017

(54) HYDROFORMYLATION OF TRIGLYCERIDES IN A SELF-EMULSIFYING MEDIUM

(71) Applicants: PIVERT, Venette (FR); CENTRE NATIONAL DE LA RECHERCHE SCIENTIFIQUE (CNRS), Paris (FR); UNIVERSITE D'ARTOIS, Arras (FR)

(72) Inventors: Frédéric Hapiot, Ennevelin (FR); Eric Monflier, La Madeleine (FR); Théodore Vanbesien, Lille (FR)

(*) Notice: Subject to any disclaimer, the term of this patent is extended or adjusted under 35 U.S.C. 154(b) by 0 days.

(21) Appl. No.: 15/035,556

(22) PCT Filed: Nov. 7, 2014

(86) PCT No.: PCT/FR2014/052860
§ 371 (c)(1),
(2) Date: May 10, 2016

(87) PCT Pub. No.: WO2015/071580
PCT Pub. Date: May 21, 2015

(65) Prior Publication Data
US 2016/0289596 A1    Oct. 6, 2016

(30) Foreign Application Priority Data
Nov. 12, 2013    (FR) ..................................... 13 61018

(51) Int. Cl.
C07C 51/10    (2006.01)
C11C 3/00    (2006.01)
C07C 67/313    (2006.01)

(52) U.S. Cl.
CPC .............. C11C 3/00 (2013.01); C07C 67/313 (2013.01)

(58) Field of Classification Search
CPC ................................. C11C 3/00; C07C 67/313
USPC ......................................................... 554/128
See application file for complete search history.

(56) References Cited

U.S. PATENT DOCUMENTS 5,847,228 A    12/1998    Monflier et al.
2004/0176265 A1    9/2004    Milius et al.

FOREIGN PATENT DOCUMENTS

| FR | 2729385 A1 * | 7/1996 | ............. C07C 45/49 |
| FR | 2729385 A1 | 7/1996 | |
| WO | WO-02100524 A1 | 12/2002 | |
| WO | WO 2008156993 A2 * | 12/2008 | ........... C07C 67/347 |
| WO | WO-2008156993 A2 | 12/2008 | |

OTHER PUBLICATIONS

Franke et al : "Applied Hydroformylation", Chemical Reviews, vol. 112, No. 11, Nov. 14, 2012, pp. 5675-5732.*

(Continued)

*Primary Examiner* — Deborah D Carr
(74) *Attorney, Agent, or Firm* — Winstead PC (57) ABSTRACT

The invention relates to a method for the hydroformnylation of triglycerides by homogeneous catalysis in the presence of at least one substituted cyclodextrin, said method comprising a step a) of combining, under agitation, at least one catalyst, waiter, at least one unsaturated triglyceride and said substituted cyclodextrin, in the presence of gaseous hydrogen and carbon monoxide, said step being carried out in reactive conditions allowing the formation of an emulsion during the agitation and a decanting of the products once the agitation has stopped.

18 Claims, 2 Drawing Sheets

(56) References Cited

OTHER PUBLICATIONS

Hapiot et al: "Rhodium-catalyzed hydroformylation promoted by modified cyclodextrins : Current scope and future developments", Current Organic Synthesis, vol. 5, No. 2, May 1, 2008, pp. 162-172.*

Salager, Jean-Louis, et al.; "Formulation des émulsions par la méthode du HLD"; Techniques de l'Ingénieur, vol. Génie des Procédés, J2-158,; Sep. 10, 2006; pp. 1-15.

Brochette, Pascal; "Émulsification—Élaboration et étude des émulsions"; Techniques de l'Ingénieur, J2150 V2; Dec. 10, 2013; pp. 1-28.

Duval, Eric, "International Search Report," prepared for PCT/FR2014/052860, as mailed Feb. 13, 2015, three pages.

Franke, Robert, et al., "Applied Hydroformylation," Chemical Reviews, vol. 112, No. 11, Aug. 31, 2012, pp. 5675-5732.

Hapiot, Frédéric, et al., "Rhodium-Catalyzed Hydroformylation Promoted by Modified Cyclodextrins: Current Scope and Future Developments," Current Organic Synthesis, Bentham Science Publishers Ltd., vol. 5, No. 2, May 1, 2008, pp. 162-172.

Legrand, François-Xavier, et al.; "Aqueous Hydroformylation Reaction Mediated by Randomly Methylated β-Cyclodextrin: How Substitution Degree Influences Catalytic Activity and Selectivity," Journal of Molecular Catalysis A: Chemical (2009), vol. 303, No. 1-2, Jan. 8, 2009, pp. 72-77.

Leclercq, Loïc, et al., "Biphasic Aqueous Organometallic Catalysis Promoted by Cyclodextrins: Can Surface Tension Measurements Explain the Efficiency of Chemically Modified Cyclodextrins?," Journal of Colloid and Interface Science (2007), vol. 307, No. 2, Dec. 8, 2006, pp. 481-487.

Leclercq, Loïc, et al., "Versatile Eco-Friendly Pickering Emulsions Based on Substrate/Native Cyclodextrin Complexes: A Winning Approach for Solvent-Free Oxidations," ChemSusChem (2013), vol. 6, No. 8, Jun. 21, 2013, pp. 1533-1540.

Shimada, Kazuko, et al., "Structure of Inclusion Complexes of Cyclodextrins With Triglyceride at Vegetable Oil/Water Interface," Journal of Food Science (1992), vol. 57, No. 3, May 1992, pp. 655-656.

* cited by examiner

HYDROFORMYLATION OF TRIGLYCERIDES IN A SELF-EMULSIFYING MEDIUM

TECHNICAL FIELD

The invention relates to a process for the hydroformylation of triglycerides by creating systems allowing temporary self-emulsification of the reaction medium.

PRIOR ART

The vegetable oil hydroformylation reaction is of major interest from the viewpoint of the numerous applications of the reaction products that it provides. The aldehydes thus formed are used in the industrial field, in particular in lubricants or plasticizers. However, the main use of these polyaldehydes remains their use in polymer chemistry, in particular for the synthesis of biobased polymers. Furthermore, hydroformylation is acknowledged to be an environmentally friendly process since it makes it possible to limit the amount of residues, or even to totally eliminate them, all the constituent atoms of the reagents being involved in the final products.

The reaction for hydroformylation of vegetable oils and of unsaturated triglycerides is carried out in the presence of a catalyst and of carbon monoxide and hydrogen gas according to the following reaction formula, where x, y and z are integers, generally ranging from 0 to 22 and where at least one of the numbers $y_1$, $y_2$ and $y_3$ is other than 0 and where, for each series $x_n$, $y_n$ and $z_n$ (n=1, 2 or 3), at least one of these numbers is greater than or equal to one:

This reaction usually takes place in a homogeneous medium and requires catalysts generally based on cobalt or on rhodium which are usually associated with ligands such as phosphines, for example triphenylphosphine (TPP).

The article "Applied Hydroformylation", Franke et al. Chemical Reviews (2012), volume 122, No. 11, p 5675-5732 describes such processes which offer good results in terms of conversion, yield and selectivity. However, the use of a homogeneous medium has a major disadvantage. This is because the recycling of the catalyst requires additional steps which are often expensive.

In order to overcome the major problem created by the recycling of the catalyst, the reaction for hydroformylation of vegetable oils and of triglycerides has been transposed to a two-phase medium. The objective is to immobilize the catalyst in a phase that is immiscible with the reagents, using for example ionic liquids or an aqueous phase. In the case of aqueous phases, additives such as surfactants or silica are required in order to promote contacts between the substrate to be converted and the catalyst. However, the use of these additives complicates the recycling of the catalyst.

In this context, it has been reported that cyclodextrins (CDs) can be effective additives in two-phase hydroformylation catalysis. FR2729385 describes the use of a rhodium catalyst such as $Rh(acac)(CO)_2$ in the presence of trisulfonated triphenylphosphine (TPPTS) and of optionally substituted CDs, for reactions for hydroformylation of linear or branched olefins of medium size in a two-phase medium without forming an emulsion. Only 1-decene is exemplified therein. At the end of the reaction, the products decant, making it possible to recover the two phases.

The article "Aqueous hydroformylation reaction mediated by randomly methylated β-cyclodextrin: How substitution degree influences catalytic activity and selectivity", F.-X Legrand et al., Journal of Molecular Catalysis A: Chemical (2009), volume 303, No. 1-2, p 72-77, studies the influence of the degree of methylation on the catalytic activity of the 1-decene hydroformylation reaction. More specifically, various types of methylated cyclodextrins present in a commercial product, RAME-β-CD, in which the average degree of substitution per glucosidic unit (DS) varies from 1.4 to 1.9, are studied therein. The increase in the catalytic activity increases proportionately to the DS, and a DS of 1.9 appears to be the most effective.

The article "Biphasic aqueous organometallic catalysis promoted by cyclodextrins: can surface tension measurements explain the efficiency of chemically modified cyclodextrins?", L. Leclerc et al., Journal of Colloid and Interface Science (2007) volume 307, No. 2, p 481-487, describes the positive effect of the methylation and of the hydroxypropylation of CDs on the interfacial tension of two-phase systems during homogeneous catalysis of the reaction for hydroformylation of short-chain olefins (for instance $C_{10}$ olefins). The cyclodextrins HP-β-CD (average DS of 0.6 and 0.8) and also RAME-β-CD (average DS 1.8) are among the CDs tested and are found to be active for hydroformylation reactions.

Inclusion complexes between organic molecules and CDs can have advantageous surfactant properties enabling the reaction system to be emulsified. In the article "Versatile Eco-friendly Pickering Emulsions Based on Substrate/Native Cyclodextrin complexes: A winning approach for Solvent-Free oxidations", Leclercq et al., ChemSusChem (2013), volume 6, No. 8, p 1533-1540, reactions for catalytic oxidation of organic substrates in the presence of native CD are described. The resulting stable emulsion is stabilized by the substrate/CD complexes having surfactant properties. The recovery of the organic phase and the recycling of the aqueous phase require centrifugation and heating steps.

The article "Structure of inclusion Complexes of Cyclodextrins with Triglyceride of vegetable Oil/Water interface", K. Shimada et al. Journal of Food science (1992) volume 57, No. 3, p 655, describes inclusion complexes formed between triglycerides and unsubstituted α-CDs or β-CDs, this being in two-phase systems. These complexes make it possible to obtain stable emulsified systems.

Furthermore, WO 02/100524 A1 also shows that fatty substance/CD complexes can have surfactant properties and that these complexes can be isolated. Triglycerides are mentioned in the list of fatty substances envisaged, but are not exemplified.

DESCRIPTION OF THE INVENTION

A process for the hydroformylation of triglycerides is now proposed, said process combining a high degree of conversion and a high selectivity while enabling great simplicity of extraction of the reaction products, this being under mild operating conditions and in an aqueous medium.

According to one embodiment, the invention relates to a process for the hydroformylation of triglycerides by homogeneous catalysis in the presence of at least one substituted cyclodextrin (CD), said process comprising a step a) of bringing together, with stirring, at least one catalyst, water, at least one unsaturated triglyceride and said substituted cyclodextrin, in the presence of hydrogen gas and of carbon monoxide, said step being carried out under reaction conditions allowing the formation of an emulsion during the stirring and decanting of the products once the stirring has stopped.

DEFINITIONS

Triglyceride: triester derived from glycerol and from three saturated or unsaturated fatty acids, having a fatty chain length which is variable but generally comprises at least 14 carbon atoms. In the context of the invention, the unsaturated triglycerides used in the process are compounds comprising more than 45 carbon atoms. The triglycerides that can be used in the process of the invention can adopt the formula previously described. Preferably, the series of numbers $x_n$, $y_n$ and $z_n$ are identical. It is also preferable for the fatty chains of the unsaturated triglycerides to each comprise at least 14 carbon atoms, preferably 16, 18 or more than 20 carbon atoms. The unsaturated triglycerides are generally very hydrophobic.

Homogeneous catalysis: catalytic process in which the catalyst is soluble in at least one liquid phase.

Cyclodextrin (CD): cyclic oligosaccharide containing respectively 6, 7 or 8 glucopyranose units (respectively called α, β or γ) which are α-(1,4)-linked. The cyclodextrins may be native (without modification) or substituted with various chemical groups of interest (methyl, hydroxypropyl, etc.) on the various hydroxyl positions of the molecule. In the latter case, the substitution may be total or partial. The degree of substitution is determined by $^1$H NMR and mass spectrometry (MALDI, electrospray).

Reaction conditions: operating conditions under which the reaction takes place. These conditions are, for example, the concentrations and/or the relative proportions of the reagents brought together and also the physical characteristics of the medium, such as the pressure, the temperature and the stirring.

Emulsion: macroscopically homogeneous, microscopically heterogeneous dispersion of two immiscible substances, the stability of which varies over time.

Normal stirring conditions: the reaction system is stirred mechanically in a range of 400 to 1400 revolutions/minute. The stirring speed is generally set at its maximum value for optimal dispersion of the organic phase in the aqueous phase.

Rapid decanting: one of the particularly advantageous aspects of the invention is rapid decanting, i.e. separation of the aqueous and oily (organic) phases in less than one hour, preferably in less than 30 min and advantageously in less than 10 min (for example less than 5 min).

Determination of the Conditions for Obtaining an Emulsion that is Active in Catalysis In order to be able to determine the conditions for obtaining an emulsion which makes it possible to carry out the invention, it is advisable to study the self-emulsifying capacity of the CD/triglycerides pair and to thus have a macroscopic idea of the state of the water/triglyceride/CD system. A known experimental method is to establish a phase diagram by observing a series of mixtures of which only the respective proportions of CD, of triglycerides and of water vary and fixing the other conditions, such as the pressure, the temperature, the stirring, etc. Once the stirring has stopped, the change in the medium is then observed over time. These experiments make it possible to determine by observation the range of proportions of the reagents to be used for the given conditions which make it possible to obtain the required emulsion, which range should be used for carrying out the invention. The extent of these ranges depends on the period of time after which the system is observed after stirring. A period of two minutes was chosen in order to be able to evaluate the state of the water/oil/CD system under conditions judged to be close to the initial conditions of the catalysis, i.e. with temperatures ranging from 25 to 100° C., preferably 80° C., and stirring at 1400 rpm. Thus, for a triglyceride such as triolein, the following domains were observed:

Domain A: two distinct phases, an aqueous phase and an oily phase

Domain B: emulsion (oil-in-water)+an aqueous phase

Domain C: phase comprising a solid in suspension

Domain D: emulsion (oil-in-water)

Domain B is the one which should be used for carrying out the reaction since it makes it possible to obtain phase separation at the end of the reaction. The conditions of domain A do not make it possible to obtain an effective hydroformylation reaction. Likewise, it is possible to produce phase diagrams for hydroformylation reaction conditions other than the respective concentrations of the reagents. These other conditions may be, for example, the temperature or the pressure of the mixture. The production of phase diagrams is well known and formalized and is part of the basic knowledge of those skilled in the art. For example, the reference articles published by Techniques De l'Ingénieur [Expert's Techniques] j2150, entitled "Emulsion—Elaboration et étude des émulsions" ["Emulsion—Production and study of emulsions"] and published on Dec. 12, 2013, on the one hand, and j2158, entitled "Formulation des emulsions par la méthode du HDL" ["Formulation of emulsions by the HDL method"], Sep. 10, 2006, on the other hand, clearly establish that this technique is perfectly known and controlled.

According to one preferred embodiment of the invention, the substituted cyclodextrin used is an α-, β- or γ-cyclodextrin. Preferably, said cyclodextrin is a β- or γ-cyclodextrin.

It is also preferred for the substituted cyclodextrin to be a methylated and/or hydroxypropylated cyclodextrin. Thus, the cyclodextrin used in the process according to the invention is advantageously chosen from the group consisting of RAME-β-CD, HP-α-CD, HP-β-CD, HP-γ-CD, RAME-γ-CD, CRYSMEB and mixtures thereof.

The average degree of substitution of the substituted cyclodextrin can be chosen in a range of from 0.5 to 3, preferably of from 0.5 to 2.0. When the cyclodextrin is a methylated cyclodextrin, an average degree of substitution of approximately 1.8±10% or of 0.8±10% is particularly advantageous. When the substituted cyclodextrin is a hydroxypropylated cyclodextrin, an average degree of substitution ranging from 0.5 to 0.9, preferably from 0.5 to 2.0, for instance 0.6 or 0.8, is particularly advantageous.

According to one particular embodiment of the process according to the invention, step a) is carried out at a temperature chosen in the range of from 40 to 140° C., preferably from 40° C. to 120° C., more particularly from 50 to 70° C. A temperature in the region of 60° C. or of 80° C., ±5° C., is preferred.

It is also preferred for the cyclodextrin/triglyceride mole ratio to be chosen in a range of from 0.5 to 3.0, preferably of from 0.2 to 4.0, in the region of 2.9.

According to one preferred aspect of the invention, step a) is carried out under pressure of a gas which comprises molecular hydrogen and carbon monoxide. Step a) of the process according to the invention may advantageously be carried out under pressure of a gas comprising molecular hydrogen and/or carbon monoxide, said gas pressure preferably being greater than or equal to 20 bar. Advantageously, said pressure is chosen in a range of from 20 to 200 bar. Preferably, the pressure is greater than or equal to 80 bar.

Preferably, the catalyst of the reaction comprises, or consists of, a transition metal such as rhodium, ruthenium, palladium, iridium, cobalt and platinum, or a bimetallic compound such as platinum/tin and platinum/iron. Particularly advantageously, this catalyst is in the form of a complex combined with a phosphine, which is optionally sulfonated and/or water-soluble, such as TPPTS or a sulfonated phenyl(s)/biphenyl(s) phosphine.

The phosphine may be a water-soluble phosphine corresponding to the general formula below:

in which:
A, B and C, which may be identical or different, each represent an aryl group chosen from phenyl groups, naphthyl groups and biphenyl groups or from alkyl groups having from 1 to 10 carbon atoms;
the substituents $R^1$, $R^2$ and $R^3$, which may be identical or different, each represent a group chosen from hydrogen, alkyl radicals having from 1 to 4 carbon atoms, alkoxy radicals having from 1 to 4 carbon atoms, halogen atoms, and the groups —CN, —NO$_2$, —OH and —N(Z1)(Z2), Z1 and Z2, which may be identical or different, each representing an alkyl radical having from 1 to 5 carbon atoms;
the substituents $X^1$, $X^2$ and $X^3$, which may be identical or different, each represent a carboxylic acid group, a sulfonic acid group or salts thereof. When $X^1$, $X^2$ or $X^3$ represents a carboxylic or sulfonic acid salt, the cation may be an alkali metal cation or alkaline-earth metal cation or an ammonium cation of formula $N(T^1T^2T^3T^4)^+$ in which $T^1$, $T^2$, $T^3$ and $T^4$, which may be identical or different, each represent an alkyl group comprising from 1 to 4 carbon atoms;
x1, x2 and x3 are numbers, which may be identical or different, ranging between 0 and 3 inclusive, at least one of them being greater than or equal to 1;
y1, y2 and y3 are numbers, which may be identical or different, which can range between 2 and 9 inclusive.

Preferably, A, B and C each represent an aryl group, more particularly a phenyl or biphenyl group. The substituents $X^1$ to $X^3$ are advantageously —SO$_3$Na or —CO$_2$Na. The substituents $R^1$ to $R^3$ are advantageously hydrogen or an alkyl group. The numbers x1, x2 and x3 are advantageously equal to 1 or 0 (at least one of them being equal to 1). The numbers y1, y2 and y3 can range between 4 and 9.

By way of examples, mention may be made of trisulfonated triphenylphosphine (TPPTS) (A=B=C=phenyl; $R^1=R^2=R^3$=H; $X^1=X^2=X^3$=SO$_3$Na; x1=x2=x3=1; y1=y2=y3=4) and trisulfonated biphenyldiphenylphosphine (A=B=phenyl; C=biphenyl; $R^1=R^2=R^3$=H; $X^1=X^2=X^3$=SO$_3$Na; x1=x2=x3=1; y1=y2=4; y3=8).

The sulfonated phosphines which are particularly advantageous for the process of the present invention are TPPTS and sulfonated phenyl(s)-biphenyl(s) phosphines.

According to one preferred aspect of the invention, said unsaturated triglyceride is a mixture of triglycerides, which mixture advantageously does not comprise more than 25 mol %, preferably not more than 15 mol % and more particularly not more than 10 mol % of polyunsaturated fatty chains in the triglycerides, i.e. of carbon-based chains comprising at least two C=C double bonds.

The unsaturated triglyceride is preferably a triglyceride comprising an average number of C=C double bonds of less than or equal to 3.5 and preferably less than or equal to 3. This number may for example range from 1 to 3, preferably from 2 to 2.90 and in particular from 2.7 to 2.8.

The process according to the invention may be carried out using a biobased oil, such as refined or unrefined vegetable oils, for example oleaginous oils. The vegetable oils may for example be olive oil, sesame oil, soybean oil, sunflower oil or rapeseed oil. Preferably, these oils may be olive oil or sunflower oil.

According to one particularly advantageous aspect of the invention, step a) is carried out in the absence of organic solvent, and in particular without organic compounds not participating in the reaction and/or being present at more than 10% by weight in the reaction medium. Preferably, since said decanting allows the separation of an organic phase containing the reaction products, the step of recovering the reaction products is carried out by separation of the reaction medium from said phase.

The amount of water of the reaction medium is preferably greater than or equal to 50% by weight of the reaction medium. For some CDs, with low methylation (for example a degree of 0.8), it may be advantageous to use a concentration range greater than or equal to 65% by weight of water, for example 72% by weight. Quite obviously, it is advisable to use a concentration range which allows decanting of the reaction products while at the same time avoiding excessive dilution of the products (for example an amount of water of greater than 75% by weight).

The reaction time may range from a few minutes to several days according to the reaction conditions. It is generally several hours, but is generally less than 24 hours.

It may be chosen between 2 and 20 hours, advantageously between 4 and 19 hours, for example 6 or 18 hours.

According to another embodiment, the invention relates to the use of at least one of the abovementioned modified cyclodextrins in a process for the hydroformylation of the triglycerides, as previously described.

BRIEF DESCRIPTION OF THE DRAWINGS

The invention will be understood more clearly on reading the appended figures, which are provided by way of examples and are in no way limiting in nature, in which.

DETAILED DESCRIPTION OF THE INVENTION

Example 1

Figure 1:
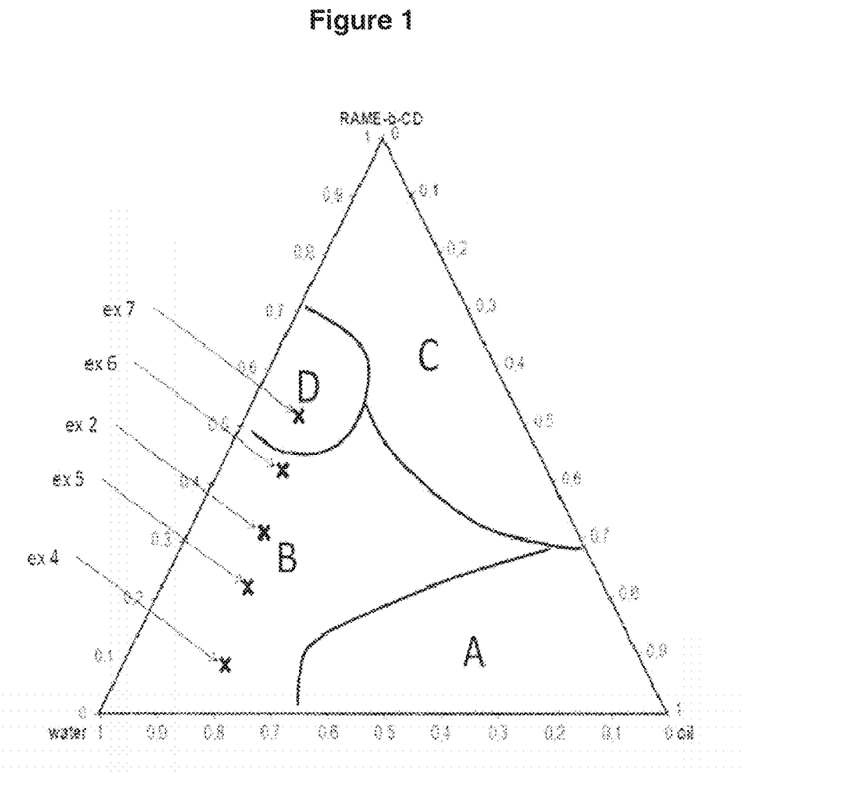
FIG. 1: is a phase diagram at 80° C. of a water/triolein/RAME-β-CD system two minutes after the stirring has stopped.

Production of the Phase Diagram for the Water/Triolein/Substituted Cyclodextrin (CD) System at t=2 Min This diagram is produced by varying the weight proportions between the components. The results are presented in FIG. 1. The proportions are calculated in the following way:

$$\%(i) = \frac{w_i}{w_{total}} = \left( \frac{w_i}{w_{CD} + w_{water} + w_{triolein}} \right)$$

$w_i$ being the weight of the compound of which it is desired to determine the proportion.

Since emulsions are temperature-dependent, the diagram was produced at a temperature of 80° C. (temperature used for the catalytic tests). The procedure used is the following:

Predetermined amounts of RAME-β-CD and of triolein (cf. Table 1a, tubes 1 to 4) are placed in a test tube equipped with a magnetic stirrer. A certain amount of water is then added to each tube. The medium is left to stir (magnetic bar at 1400 revolutions/min) in an oil bath at 80° C. for 20 min.

The stirring is then stopped. Two minutes after the stirring has stopped, the test tube is removed from the bath for observation. Once the phases have been identified, a further amount of water is added, thus changing the proportions of the various constituents.

The operations described above are repeated until obtaining of the results presented in table 1b which are plotted on the phase diagram and make it possible to determine the following domains A, B, C and D:

Domain A: two distinct phases, an aqueous phase and an oily phase

Domain B: emulsion (oil-in-water)+an aqueous phase

Domain C: phase comprising a solid in suspension

Domain D: emulsion (oil-in-water)

TABLE 1a

| | Total weight water (g) | Weight CD (g) | Weight oil (g) |
|---|---|---|---|
| Tube 1 | | 0.1 | 0.36 |
| Tube 2 | | 0.3 | 0.46 |
| Tube 3 | | 0.5 | 0.27 |
| Tube 4 | | 0.7 | 0.14 |

TABLE 1b

| | Example 1 | | | | | | | | | | |
|---|---|---|---|---|---|---|---|---|---|---|---|
| | Total weight water (g) | | | | | | | | | | |
| | 0.1 | 0.2 | 0.3 | 0.4 | 0.6 | 0.8 | 1 | 1.4 | 1.8 | 2.2 | 3.6 |
| Domains | A | A | A | A | A | B | B | B | B | B | B |
| | C | D | B | B | B | B | B | B | B | B | B |
| | C | C | B | B | B | B | B | B | B | B | B |
| | C | C | D | D | D | B | B | B | B | B | B |

Example 2

Reaction for Hydroformylation of a Triglyceride, Triolein, in a Self-Emulsifying System According to the Invention The reaction scheme is the following:

Triolein 6.2 ml of an aqueous solution containing 3.05 mmol (4 g) of partially methylated β-cyclodextrins (RAME-β-CD) having an average molar mass of 1310 g·mol$^{-1}$ and an average degree of substitution of 1.8 per glucoside unit, 0.029 mmol (7.5 mg) of (acetylacetonato)dicarbonyl rhodium(I) and 0.15 mmol (85 mg) of tri(meta-sulfonatophenyl)phosphine trisodium salt are placed in a 25 ml autoclave containing 1.9 mmol (1.8 ml) of triolein (i.e. 5.8 mmol of internal C=C double bonds).

This system corresponds to the proportions given in FIG. 1 on the phase diagram. The autoclave is heated to 80° C., pressurized under 50 bar of a CO/H$_2$ mixture in equimolar proportion, and the stirring is regulated at 1400 revolutions/minute for 18 hours.

After the stirring has stopped, an emulsified phase containing the oil (initial products and reaction products) in the water and an aqueous phase are observed. Five minutes after the stirring has stopped, the emulsified phase has completely decanted, allowing the extraction of the organic phase and the recycling of the aqueous phase containing the catalyst and the CDs.

A conversion of 26% and a selectivity of 78% in favor of the aldehyde are determined by NMR of the reaction products after decanting of the latter. This conversion corresponds to a conversion of the unsaturations contained in the triolein and not a conversion of the triolein itself.

Aldehyde selectivity: number of moles of aldehyde formed/number of moles of initial olefins that have been converted.

Examples 3 to 7

Influence of the Amount of Substituted CD on the Hydroformylation Reaction of Example 2

These examples were carried out under the same experimental conditions in terms of time, pressure and temperature and also with the same catalytic agents as example 2. They show the influence of the amount of CD on the hydroformylation reaction.

The relative positions of examples 4 to 7 on the phase diagram previously produced are given in FIG. 1. Experiment 3 is an example without cyclodextrin and is given by way of comparison. It can be shown that domain B is a zone which makes it possible to have a significant conversion and selectivity. Indeed, example 7, located in domain D, shows a decrease in the selectivity of the hydroformylation. The specific experimental conditions and also the results are collated in table 2 below.

TABLE 2

| Examples | Weight of RAME-β-CD (g) | RAME-β-CD/triglycerides mole ratio | Conversion of double bonds (%) | Aldehyde selectivity (%) |
|---|---|---|---|---|
| 3 | 0 | /// | 0 | /// |
| 4 | 0.5 | 0.20 | 5 | 62 |
| 5 | 2 | 0.82 | 19 | 84 |
| 6 | 7 | 2.88 | 39 | 78 |
| 7 | 9 | 3.71 | 35 | 44 |

Examples 8 to 12

Influence of the Temperature on the Hydroformylation Reaction of Example 2

Figure 2:
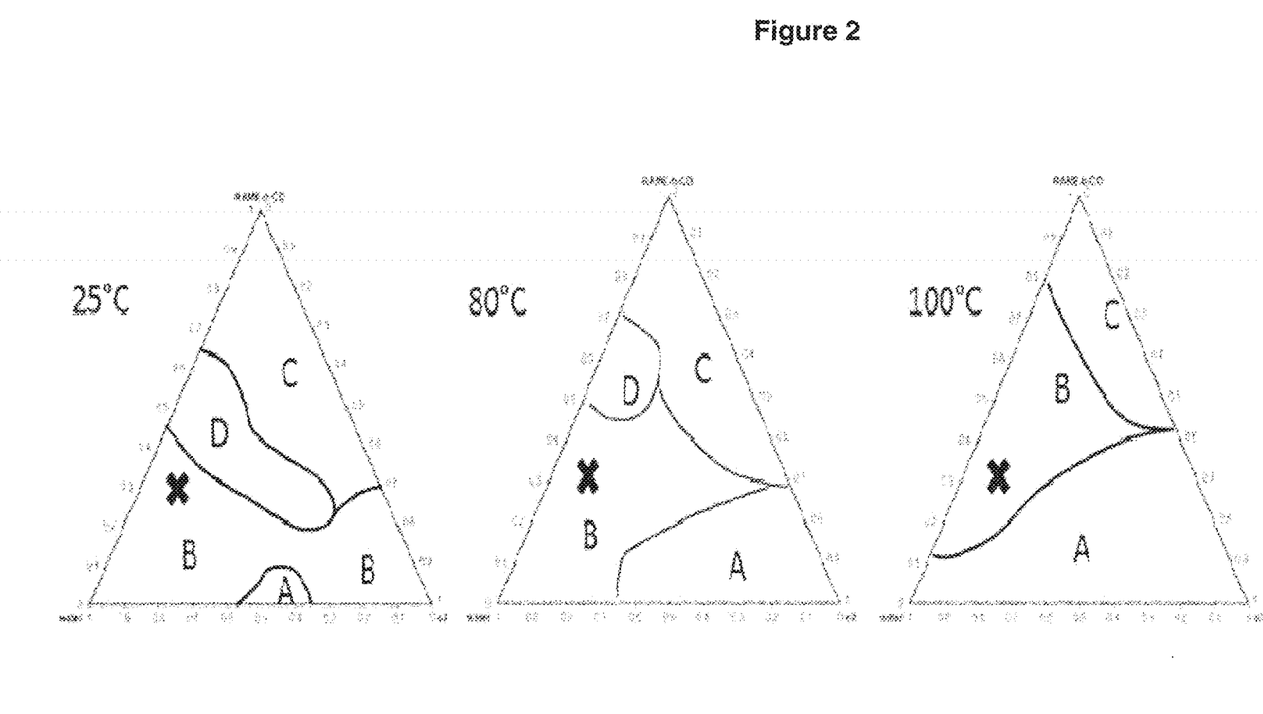
FIG. 2: shows phase diagrams of the water/triolein/RAME-β-CD system at 25° C., 80° C. and 100° C., two minutes after the stirring has stopped.

The following examples were carried out under the same experimental conditions and with the same catalytic agents as example 2. These examples show the influence of the reaction temperature on the activity of the catalytic system inherent in the invention. Since temperature influences the emulsion, several phase diagrams produced at temperatures of 25° C., 80° C. and 100° C. (at t=2 min) are represented in FIG. 2. The reaction takes place in domain B for these three temperatures. The temperature conditions and also the results are collated in table 3:

TABLE 3

| Example | Temperature (° C.) | Conversion of double bonds (%) | Aldehyde selectivity (%) |
|---|---|---|---|
| 8 | 25 | 21 | 75 |
| 9 | 40 | 47 | 90 |
| 10 | 60 | 49 | 86 |
| 11 | 100 | 21 | 48 |
| 12 | 120 | 11 | 28 |

These results show a temperature application range of between 40° C. and 80° C. with an optimum temperature at 60° C. for optimal conversion and optimal selectivity. Considering that the usual hydroformylation temperature is generally in the region of 80° C., this result is unexpected and particularly advantageous since it makes it possible to carry out the reaction under milder conditions while minimizing energy expenditure.

Examples 13 and 14

Influence of the Pressure on the Hydroformylation Reaction of Example 2

The following examples were carried out under experimental conditions identical to example 2. The following examples reflect the influence of the pressure of $CO/H_2$ syngas on conversion and selectivity. The results of these examples are collated in table 4:

TABLE 4

| Example | Pressure (bar) | Conversion of double bonds (%) | Aldehyde selectivity (%) |
|---|---|---|---|
| 13 | 20 | 12 | 25 |
| 14 | 80 | 58 | 87 |

These results show the effect of the pressure on the activity of the system inherent in the invention.

Examples 15 to 21

Comparison Between the Substituted CDs Used in the Process According to the Invention and Other Substituted CDs The following examples were carried out with various native or substituted CDs under the same experimental conditions as example 2 and after verification that these reaction conditions are those located in domain B and therefore make it possible to obtain an emulsion. They make it possible to show the influence of the cyclodextrin and of the chemical modifications made thereto on the conversion (Cony) and the aldehyde selectivity (Selec). The results are collated in table 5.

TABLE 5

| Example | Modification $DS^c$ | Weight$_{CD}$ (%)$^d$ | T (° C.) | P (bar) | Conv (%) | Selec (%) | Decanting |
|---|---|---|---|---|---|---|---|
| 15 | α-CD | // | 5 | 80 | 50 | >2 | /// | No |
| 16 | β-CD | // | 7 | 80 | 50 | 3 | /// | No |
| 17 | RAME-β-CD$^a$ | 1.8 | 34 | 80 | 80 | 58 | 87 | Yes |
| 18 | RAME-β-CD | 1.8 | 34 | 80 | 80 | 32 | 76 | Yes |
| 19 | HP-α-CD$^b$ | 0.6 | 34 | 80 | 80 | 29 | 81 | Yes |
| 20 | HP-β-CD$^b$ | 0.8 | 34 | 80 | 80 | 98 | 90 | Yes |
| 21 | HP-β-CD$^b$ | 0.6 | 34 | 80 | 80 | 95 | 89 | Yes |
| 22 | HP-γ-CD$^b$ | 0.6 | 34 | 80 | 80 | 86 | 90 | Yes |

$^a$corresponds to a partially methylated cyclodextrin
$^b$corresponds to a cyclodextrin partially substituted with a 2-(hydroxypropyl) group
$^c$DS: degree of substitution per glucoside unit
$^d$weight proportion of the cyclodextrin in question in the reaction medium

Examples 23 to 27

Process for Hydroformylation on a Mixture of Triglycerides of Natural Origin: Commercial Olive Oil The following examples were carried out under the same conditions as example 2. As in the previous examples, it was verified beforehand that the system is in a domain of type B by producing the phase diagrams. Decanting after reaction is observed for the commercial oil, and for the triolein. These vegetable oils are not pure, but the following results make it possible to state that the present invention is suitable for the hydroformylation of complex mixtures of triglycerides. The results are collated in table 6.

TABLE 6

| Example | Cyclodextrin | Pressure (bar) | Temperature (° C.) | Time (hours) | Conversion (%) | Selectivity (%) |
|---|---|---|---|---|---|---|
| 23 | RAME-β-CD (1.8)$^a$ | 50 | 80 | 18 | 44 | 56 |
| 24 | RAME-β-CD (1.8)$^a$ | 80 | 80 | 18 | 66 | 70 |
| 25 | RAME-β-CD (1.8)$^a$ | 100 | 50 | 6 | 35 | 78 |
| 26 | RAME-β-CD (1.8)$^a$ | 150 | 50 | 6 | 58 | 81 |
| 27 | HP-β-CD (0.6)$^a$ | 80 | 80 | 18 | 78 | 85 |

$^a$The number between parentheses represents the degree of substitution per glucoside unit of the cyclodextrin in question.

The commercial oil used for these examples was analyzed by trans-esterification of the triglycerides in methanol and by gas chromatography in order to determine the various fatty acid derivatives making up the vegetable oil. The results are collated in table 7:

TABLE 7

| Fatty acid[a] | Molar proportion in olive oil (%) |
|---|---|
| Palmitoleic acid ($C_{16:1}$) | 0.7 |
| Palmitic acid ($C_{16:0}$) | 11.1 |
| Stearic acid ($C_{18:0}$) | 3.2 |
| Oleic acid ($C_{18:1}$) | 76.7 |
| Linoleic acid ($C_{18:2}$) | 4.1 |

TABLE 7-continued

| Fatty acid[a] | Molar proportion in olive oil (%) |
|---|---|
| Linolenic acid ($C_{18:3}$) | 1.7 |
| Arachidic acid ($C_{20:0}$) | 2.5 |

[a]The abbreviations between parentheses make it possible to schematize the type of fatty acid. The first number represents the total number of carbon atoms of the fatty acid, the second number indicating the number of unsaturations on the carbon-based chain.

Examples 28 to 31

Influence of the Nature of the Phosphine

The following examples were carried out according to the same experimental conditions as example 2, except for the nature of the phosphine used in combination with rhodium and also the $CO/H_2$ syngas pressure, which is 80 bar. In these examples, a sulfonated monophosphine with a phosphine/metal mole ratio of 5/1 is used. The phosphines used and also the effects of the latter on the hydroformylation reaction are given in table 8:

TABLE 8

| Example | Phosphine | Phosphine structure | Conversion (%) | Selectivity (%) |
|---|---|---|---|---|
| 28 | Disulfonated tris(o-toluyl) phosphine | | 91 | 88 |
| 29 | Trisulfonated biphenyldiphenyl phosphine | | 58 | 85 |
| 30 | Trisulfonated bis(biphenyl)phenyl phosphine | | 72 | 86 |

TABLE 8-continued

| Example | Phosphine | Phosphine structure | Conversion (%) | Selectivity (%) |
|---|---|---|---|---|
| 31 | Trisulfonated tris(biphenyl) phosphine | [structure: phosphine with three biphenyl groups each bearing SO₃Na, central P bonded to a fourth biphenyl-SO₃Na] | 51 | 82 |

The phosphines that are particularly advantageous in the process of the present invention are TPPTS and sulfonated phenyl(s)-biphenyl(s) phosphines, i.e. sulfonated phosphines comprising phenyl groups and/or biphenyl groups. The examples listed in table 8 make it possible to show the validity of the present invention for a range of sulfonated aromatic phosphines.

Example 32

Influence of the Temperature for HP-β-CD

The presence of an optimum temperature for HP-β-CD is established using the procedure of example 2 under the following specific reaction conditions: % by weight of the various constituents: HP-β-CD: 34%, water: 54%, oil: 17%, 80 bar $CO/H_2$, 18 hours, 1 mmol of triolein (3 mmol of double bonds), mole ratio: double bond/Rh=200; phosphine/Rh mole ratio=5. The catalyst and the phosphine are those of example 2. A phase separation clearly takes place. The results presented in table 9 were obtained using the analytical methods previously described.

TABLE 9

| Temperature (° C.) | Conversion of double bonds (%) | Aldehyde selectivity (%) |
|---|---|---|
| 30 | 28 | 68 |
| 50 | 53 | 79 |
| 60 | 69 | 85 |
| 80 | 91 | 90 |
| 100 | 55 | 65 |
| 120 | 13 | 23 |

Example 33

Influence of the Weight Concentration of HP-β-CD

The role of the weight concentration of HP-β-CD in the reaction is established using the procedure of example 2 under the following specific reaction conditions: water: 3.4 ml, pressure 80 bar $CO/H_2$, stirring time 18 hours, 1 mmol of triolein (3 mmol of double bonds), double bond/Rh mole ratio=200, phosphine/Rh mole ratio=5. The catalyst and the phosphine are those of example 2. A phase separation clearly takes place except when the CD concentration is outside the desired phase separation domain. The results presented in table 10 were obtained using the analytical methods previously described.

TABLE 10

| % by weight of CD | Conversion of double bonds (%) | Aldehyde selectivity (%) | Decanting |
|---|---|---|---|
| 44 | 87 | 89 | No |
| 34 | 91 | 90 | Yes |
| 20 | 61 | 84 | Yes |
| 12 | 43 | 70 | Yes |
| 7 | 23 | 59 | Yes |

These results indicate that, since phase separation conditions which allow decanting are used, the higher the amount of cyclodextrin, the higher the degrees of conversion and of selectivity.

Example 34

Hydroformylation Process Using HP-β-CD on Olive Oil, Validation of the Temperatures and of the Weight Concentrations of the Mixture The role of 1) the temperature, 2) the weight concentration of HP-β-CD and 3) the weight concentration of water (at constant HP-β-CD/oil ratio) is established using the procedure of example 2.

1) For the temperature, the specific reaction conditions are the following: % by weight: HP-β-CD: 34%, water: 54%, oil: 17%, pressure 80 bar $CO/H_2$, stirring time 18 hours, 1 mmol of commercial olive oil, double bond/Rh mole ratio=200, phosphine/Rh mole ratio=5. The catalyst and the phosphine are those of example 2. A phase separation clearly takes place. The results presented in table 11 were obtained using the analytical methods previously described.

TABLE 11

| Temperature (° C.) | Conversion of double bonds (%) | Aldehyde selectivity (%) |
| --- | --- | --- |
| 30 | 28 | 68 |
| 50 | 50 | 79 |
| 60 | 55 | 80 |
| 80 | 78 | 85 |
| 100 | 48 | 65 |
| 120 | 12 | 23 |

Thus, an optimum temperature of around 80° C. is established.

2) For the weight concentration of HP-β-CD, the specific reaction conditions are the following: water: 3.4 ml, pressure 80 bar $CO/H_2$, stirring time 18 hours, 1 mmol of commercial olive oil, double bond/Rh mole ratio=200, phosphine/Rh mole ratio=5. The catalyst and the phosphine are those of example 2. A phase separation clearly takes place except when the CD concentration is outside the desired phase separation domain. The results presented in table 12 were obtained using the analytical methods previously described.

TABLE 12

| % by weight of CD | Conversion of double bonds (%) | Aldehyde selectivity (%) | Decanting |
| --- | --- | --- | --- |
| 44 | 81 | 76 | No |
| 34 | 78 | 85 | Yes |
| 20 | 51 | 72 | Yes |
| 12 | 38 | 70 | Yes |
| 7 | 23 | 56 | Yes |

These results indicate that, since phase separation conditions which allow decanting are used, the higher the amount of cyclodextrin, the higher the degrees of conversion and of selectivity.

3) For the weight concentration of water (constant HP-β-CD/olive oil weight ratio equal to 2), the specific reaction conditions are the following: 2.3 g of HP-β-CD, 1.1 ml of commercial olive oil, pressure 80 bar $CO/H_2$, stirring time 18 hours, double bond/Rh mole ratio=200, phosphine/Rh mole ratio=5. The catalyst and the phosphine are those of example 2. A phase separation clearly takes place except when the amount of water is outside the desired phase separation domain. The results presented in table 13 were obtained using the analytical methods previously described.

TABLE 13

| % by weight of water | Conversion of double bonds (%) | Aldehyde selectivity (%) | Decanting |
| --- | --- | --- | --- |
| 24 | 3 | 43 | No |
| 39 | 19 | 54 | No |
| 52 | 78 | 85 | Yes |
| 66 | 74 | 83 | Yes |
| 79 | 66 | 77 | Yes |
| 88 | 55 | 65 | Yes |

These results indicate that, since phase separation conditions which allow decanting are used, the optimum amount of water is less than 79% by weight.

Example 35

Hydroformylation Process Using CRYSMEB on Triolein

CRYSMEB is a β-cyclodextrin methylated in position 2 with a low degree of substitution ($DS_{CRYSMEB}$=0.8 compared with $DS_{RAMEB}$=1.8). This cyclodextrin was tested beforehand under the emulsion condition. It makes it possible to obtain emulsions that are slightly more stable (slightly slower decanting) but all the same allow decanting of the oil after a resting time without stirring of about a few minutes.

The presence of an optimum temperature for CRYSMEB is established using the procedure of example 2 under the following specific reaction conditions: % by weight of the various constituents: CRYSMEB 20%, water: 71%, oil: 9% (1 mmol of triolein (3 mmol of double bonds)), pressure 80 bar $CO/H_2$, stirring time 6 hours, mole ratio: double bond/Rh=200; phosphine/Rh mole ratio=5. The catalyst and the phosphine are those of example 2. A phase separation clearly takes place. The results presented in table 14 were obtained using the analytical methods previously described.

TABLE 14

| Temperature | Conversion of double bonds (%) | Aldehyde selectivity (%) |
| --- | --- | --- |
| 40 | 69 | 87 |
| 60 | 96 | 88 |
| 80 | 96 | 94 |
| 100 | 74 | 84 |
| 120 | 36 | 70 |

Thus, an optimum temperature in the region of 60 to 80° C. is established.

The role of the weight concentration of CRYSMEB in the reaction is established using the procedure of example 2 under the following specific reaction conditions: water: 8.0 ml, temperature: 80° C., pressure 80 bar $CO/H_2$, stirring time 6 hours, 1 mmol of triolein (3 mmol of double bonds), double bonds/Rh=200, phosphine/Rh=5. The catalyst and the phosphine are those of example 2. A phase separation clearly takes place. The catalyst and the phosphine are those of example 2. A phase separation clearly takes place except when the CD concentration is outside the desired phase separation domain. The results presented in table 15 were obtained using the analytical methods previously described.

TABLE 15

| % by weight of CD | Conversion of double bonds (%) | Aldehyde selectivity (%) | Decanting |
| --- | --- | --- | --- |
| 25 | 94 | 94 | No |
| 20 | 96 | 94 | Yes |
| 11 | 79 | 97 | Yes |
| 6 | 61 | 85 | Yes |
| 3 | 41 | 82 | Yes |
| 0 | <1 | /// | Yes |

The study according to the weight proportion of CD shows that the more the amount of CD increases in the medium, the more the conversion and the selectivity increase. The increase in the CD concentration would allow the formation of more inclusion complexes by shifting the equilibrium in favor of the formation of the latter. Since the number of surfactant complexes increases, the emulsion that results therefrom would be more stable, and more homogeneous with a maximum interface. However, it should be noted that, beyond a certain weight of CD, the conversion no longer changes and the selectivity begins to decrease. Furthermore, the emulsion increasingly stabilizes with the proportion of CD, which is of course to be avoided.

Example 36

Process for the Hydroformylation of Sunflower Oil

The process is carried out using sunflower oil and three cyclodextrins previously described. The experimental protocol is the same as that of example 2, under the following specific conditions:

[a] Conditions: CD (2.3 g), oil (1 ml, 1 mmol), Rh((CO))$_2$ (acac) (3.9 mg, 0.015 mmol), TPPTS (42 mg, 0.075 mmol), water (5 ml), CO/H$_2$ pressure=80 bar, temperature=80° C., stirring time 18 h.

[b] Conditions: CD (2.3 g), oil (1 ml, 1 mmol), Rh((CO))$_2$ (acac) (3.9 mg, 0.015 mmol), TPPTS (42 mg, 0.075 mmol), water (8 ml), CO/H$_2$ pressure=80 bar, temperature=80° C., stirring time 6 h.

The results obtained were compiled with those previously obtained for olive oil, for the purposes of comparison, in table 16:

| Entry | CD | Oil | Number of initial C=C double bonds | Conversion of C=C double bonds (%) | Aldehyde selectivity (%) | Initial % of polyunsaturate in the oil | % of isomerization of the polyunsaturated chains |
|---|---|---|---|---|---|---|---|
| 1[a] | RAME-β-CD | Olive | 2.78 | 48 | 71 | 5.8 | — |
| 2[a] | HP-β-CD | Olive | 2.78 | 78 | 85 | 5.8 | — |
| 3[a] | HP-β-CD | Sunflower | 2.75 | 51 | 80 | 7.7 | 39 |
| 4[b] | CRYSMEB | Olive | 2.78 | 86 | 86 | 5.8 | — |
| 5[b] | CRYSMEB | Sunflower | 2.75 | 54 | 80 | 7.7 | 52 |

Number of initial C=C double bonds: average number of C=C double bonds initially present in the triglycerides making up the oil comprising all types of unsaturations (monounsaturated+polyunsaturated). Number of unsaturations of the plant oils determined by $^1$H NMR.

Initial % of polyunsaturates in the oil: mole percentage of fatty esters having at least two double bonds on the carbon-based chain (linoleic, linolenic derivatives) in the oil in question. Percentage obtained after methanolic transesterification of the triglycerides and GC and GC-MS analysis of the methyl esters obtained.

Percentage of isomerization of the polyunsaturated chains: number of moles of conjugated isomer formed/number of moles of initial polyunsaturated chains. It should be noted that only the polyunsaturated derivatives can be isomerized.

The invention is not limited to the embodiments presented, and other embodiments will clearly become apparent to those skilled in the art.

The invention claimed is:

1. A process for the hydroformylation of triglycerides by homogeneous catalysis in the presence of at least one substituted cyclodextrin, the process comprising:
   a step a) of bringing together, with stirring, at least one catalyst, water, at least one unsaturated triglyceride and the substituted cyclodextrin, in the presence of hydrogen gas and of carbon monoxide; and
   wherein the step is carried out under reaction conditions allowing the formation of an emulsion during the stirring and decanting of the reaction products once the stirring has stopped.

2. The process as claimed in claim 1, wherein the substituted cyclodextrin is an α, β or γ-cyclodextrin.

3. The process as claimed in claim 1, wherein the substituted cyclodextrin is a methylated cyclodextrin.

4. The process as claimed in claim 3, wherein the methylated cyclodextrin has an average degree of substitution ranging from 0.5 to 2.

5. The process as claimed in claim 1, wherein the substituted cyclodextrin is a hydroxypropylated cyclodextrin.

6. The process as claimed in claim 5, wherein the hydroxypropylated cyclodextrin has an average degree of substitution ranging from 0.5 to 2.0.

7. The process as claimed in claim 1, that wherein step a) is carried out at a temperature ranging from 40° C. to 120° C.

8. The process as claimed in claim 1, wherein the cyclodextrin/triglyceride mole ratio is chosen in a range of from 0.2 to 4.

9. The process as claimed in claim 1, wherein step a) is carried out under pressure of a gas comprising molecular hydrogen and carbon monoxide and in that the gas pressure is greater than or equal to 80 bar.

10. The process as claimed in claim 1, wherein the catalyst is a complex comprising a transition metal combined with a sulfonated phosphine.

11. The process as claimed in claim 1, wherein the triglyceride is a mixture of triglycerides, which mixture does not comprise more than 10 mol % of polyunsaturated fatty chains in the triglycerides.

12. The process as claimed in claim 1, wherein the reaction conditions are close to, or are those of, the catalysis carried out in the presence of cyclodextrin.

13. The process as claimed in claim 1, wherein the decanting allows the separation of an organic phase containing the reaction products and that the step of recovering the reaction products is carried out by separation of the reaction medium from the phase.

14. The process as claimed in claim 4, wherein the methylated cyclodextrin has an average degree of substitution of 0.8.

15. The process as claimed in claim 6, wherein the hydroxypropylated cyclodextrin has an average degree of substitution of 0.8.

16. The process as claimed in claim 7, wherein step a) is carried out at a temperature ranging from 60° C. to 80° C.

17. The process as claimed in claim 8, wherein the cyclodextrin/triglyceride mole ratio is 2.9.

18. The process as claimed in claim 10, wherein the sulfonated phosphine is selected from the group consisting of TPPTS and a sulfonated phenyl(s)/biphenyl(s) phosphine.

* * * * *

UNITED STATES PATENT AND TRADEMARK OFFICE
CERTIFICATE OF CORRECTION

PATENT NO. : 9,556,402 B2
APPLICATION NO. : 15/035556
DATED : January 31, 2017
INVENTOR(S) : Frédéric Hapiot et al.

It is certified that error appears in the above-identified patent and that said Letters Patent is hereby corrected as shown below:

| | |
|---|---|
| Column 12, Table 5, Example 18 | Replace "18  RAME-β-CD" with -- 18  RAME-γ-CD -- |
| Column 19, Lines 9-10 | Replace "Rh((CO))$_2$(acac)" with -- Rh(CO)$_2$(acac) -- |
| Column 19, Lines 13-14 | Replace "Rh((CO))$_2$(acac)" with -- Rh(CO)$_2$(acac) -- |

Signed and Sealed this
Twenty-third Day of May, 2017

Michelle K. Lee
*Director of the United States Patent and Trademark Office*